US00RE50823E

(19) United States
(12) Reissued Patent
Prchkovska et al.

(10) Patent Number: US RE50,823 E
(45) Date of Reissued Patent: Mar. 17, 2026

(54) SYSTEMS AND METHODS FOR IMPROVED TRACTOGRAPHY IMAGES

(71) Applicant: Mint Labs Inc., Duxbury, MA (US)

(72) Inventors: Vesna Prchkovska, Barcelona (ES); Paulo Reis Rodrigues, Barcelona (ES); Marc Ramos Bruach, Barcelona (ES); Pablo Villoslada, Los Altos, CA (US); Álvaro Abella de Bascarán, Oviedo (ES)

(73) Assignee: Mint Labs Inc., Duxbury, MA (US)

(21) Appl. No.: 17/858,788

(22) Filed: Jul. 6, 2022

Related U.S. Patent Documents

Reissue of:
(64) Patent No.: 10,702,156
Issued: Jul. 7, 2020
Appl. No.: 15/291,959
Filed: Oct. 12, 2016

(51) Int. Cl.
*A61B 5/00* (2006.01)
*A61B 5/055* (2006.01)
(Continued)

(52) U.S. Cl.
CPC ..... *A61B 5/0042* (2013.01); *A61B 5/055* (2013.01); *A61B 5/4064* (2013.01);
(Continued)

(58) Field of Classification Search
CPC ... A61B 5/055; A61B 5/7257; A61B 2576/00; G01R 33/56; G01R 33/543;
(Continued)

(56) References Cited

U.S. PATENT DOCUMENTS 10,702,156 B2 7/2020 Prchkovska et al.
2010/0016706 A1* 1/2010 Wohlgemuth ..... A61B 5/055 600/410

(Continued)

OTHER PUBLICATIONS

Bakshi R, Thompson AJ, Rocca MA, Pelletier D, Dousset V, Barkhof F, Inglese M, Guttmann CRG, Horsfield MA, Filippi M. MRI in multiple sclerosis: current status and future prospects. Lancet Neurol. Jul. 2008; 7(7):615-625. doi:10.1016/S1474-4422(08)70137-6.

(Continued)

*Primary Examiner* — Robert L Nasser
(74) *Attorney, Agent, or Firm* — Foley Hoag LLP; John D. Lanza

(57) ABSTRACT

The present disclosure discusses systems and methods for identifying biomarkers that can help with the diagnosis, prognosis, and treatment choices of patients with neurodegenerative diseases. Diffusion based magnetic resonance imaging can often fail for patients with a neurodegenerative disease because parameters fractional anisotropy, mean diffusivity, and radial diffusivity are based on simple models that can fail in the presence of neurodegeneration, such as demyelination. The present disclosure discusses systems and methods that enhance dMRI images and enable tractography to be performed on images of a damaged nervous system. The damaged tracks identified by the present system can be used as a biomarker for the assessment of patients. In some implementations, the biomarkers are converted into clinical scales that can be used to compare patients to one another or over time.

20 Claims, 8 Drawing Sheets

(51) Int. Cl.

| | |
|---|---|
| ***G01R 33/48*** | (2006.01) |
| ***G01R 33/50*** | (2006.01) |
| ***G01R 33/563*** | (2006.01) |
| ***G06F 19/00*** | (2018.01) |
| ***G06T 7/00*** | (2017.01) |
| ***G16H 30/20*** | (2018.01) |
| ***G16H 50/20*** | (2018.01) |

(52) U.S. Cl.
CPC ..... *A61B 5/4082* (2013.01); *G06T 7/0012* (2013.01); *G16H 30/20* (2018.01); *G16H 50/20* (2018.01); *A61B 2576/026* (2013.01); *G01R 33/4806* (2013.01); *G01R 33/50* (2013.01); *G01R 33/56341* (2013.01); *G06T 2207/10084* (2013.01); *G06T 2207/10092* (2013.01); *G06T 2207/30016* (2013.01)

(58) Field of Classification Search
CPC ..... G01R 33/5608; G01R 33/4824; G01R 33/583; A61N 2005/1055
See application file for complete search history.

(56) References Cited

U.S. PATENT DOCUMENTS

| | | | | |
|---|---|---|---|---|
| 2013/0009959 | A1* | 1/2013 | Calamante ..... | G01R 33/56341 345/428 |
| 2017/0039708 | A1* | 2/2017 | Henry ..... | A61B 5/055 |
| 2017/0261584 | A1* | 9/2017 | James ..... | G01R 33/5601 |
| 2018/0098700 | A1 | 4/2018 | Prchkovska et al. | |
| 2018/0344161 | A1* | 12/2018 | Meyer ..... | A61B 5/7485 |
| 2025/0191778 | A1 | 6/2025 | Prchkovska et al. | |

OTHER PUBLICATIONS

Non-Final Office Action on U.S. Appl. No. 15/291,959 DTD Nov. 5, 2019.

Non-Final Office Action for U.S. Appl. No. 19/063,105 dated May 15, 2025.

Audoin B, Guye M, Reuter F, Au Duong MV, Confort-Gouny S, Malikova I, Soulier E, Viout P, Chérif AA, Cozzone PJ, Pelletier J, Ranjeva JP. Structure of WM bundles constituting the working memory system in early multiple sclerosis: a quantitative DTI tractography study. Neuroimage. Jul. 15, 2007;36(4):1324-1330. Apr. 27, 2007.

Bakshi R, Thompson AJ, Rocca MA, Pelletier D, Dousset V, Barkhof F, Inglese M, Guttmann CRG, Horsfield MA, Filippi M. MRI in muliple sclerosis: current status and future prospects. Lancet Neurol. Jul. 2008; 7(7):615-625. doi:10.1016/S1474-4422(08)70137-6.

Bart Peters, Frans M. Vos, Frits H. Post, Jorik Blaas, Charl P. Botha, "Fast and Reproducible Fiber Bundle Selection in DTI Visualization", Visualization Conference, IEEE, vol. 00, No. , pp. 8, 2005, doi:10.1109/VIS.2005.40.

Bodurka J, Bandettini PA. Toward direct mapping of neuronal activity: MRI detection of ultraweak, transient magnetic field changes. Magn Reson Med. Jun. 2002;47(6):1052-1058.

Clark C. A, Werring DJ, Miller DH. Diffusion imaging of the spinal cord in vivo: estimation of the principal diffusivities and application to multiple sclerosis. Magn Reson Med. Jan. 2000;43(1):133-138.

Hagmann P, Thiran JP, Jonasson L, Vandergheynst P, Clarke S, Maeder P, Meuli R. DTI mapping of human brain connectivity: statistical fibre tracking and virtual dissection. Neuroimage. Jul. 2003;19(3):545-554.

Mori S, van Zijl PC. Fiber tracking: principles and strategies—a technical review. NMR Biomed. Nov.-Dec. 2002;15(7-8):468-480.

P. Rodrigues, R. Duits, B. M. ter Haar Romeny, and A. Vilanova. 2010. Accelerated diffusion operators for enhancing DW-MRI. In Proceedings of the 2nd Eurographics conference on Visual Computing for Biology and Medicine (EG VCBM' 10), Dirk Bartz, Charl Botha, Joachim Hornegger, Raghu Machiraju, Alexander Wiebel, and Bernhard Preim (Eds.). Eurographics Association, Aire-la-Ville, Switzerland, Switzerland, 49-56. DOI=http://dx.doi.org/10.2312/VCBM/VCBM10/049-056.

Vesna Prčkovska , Magí Andorrà, Pablo Villoslada, Eloy Martinez-Heras, Remco Duits, David Fortin, Paulo Rodrigues, Maxime Descoteaux. Contextual Diffusion Image Post-processing Aids Clinical Applications. Visualization and Processing of Higher Order Descriptors for Multi-Valued Data, Part V. 2015. 353-377. Doi: 10.1007/978-3-319-15090-1_18.

International Search Report for PCT Appln. PCT/US2017/055928 dated Dec. 7, 2017.

Klein, Jan titled "Measuring the Lesion Load of Multiple Sclerosis Patients Within the Corticospinal Tract" 7Pgs.

Kuceyeski, Amy titled "Predicting Future Brain Tissue Loss From White Matter Connectivity Disruption in Ischemic Stroke" 7 Pgs.

Prekovska, Vesna titles "Contextual Diffusion Image Post-Processing Aids Clinical Applications" 26Pgs.

Zhu, Lin titled "Lesion Load of the Corticospinal Tract Predicts Motor Impairment in Chronic Stroke" 7Pgs.

* cited by examiner

400

SYSTEMS AND METHODS FOR IMPROVED TRACTOGRAPHY IMAGES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED PATENT APPLICATION*

*This application is a Broadening Reissue of U.S. Pat. No. 10,702,156 (previously U.S. patent application Ser. No. 15/291,959) titled "SYSTEMS AND METHODS FOR IMPROVED TRACTOGRAPHY IMAGES" issued on Jul. 7, 2020, which is incorporated herein by reference in its entirety.*

BACKGROUND

Multiple sclerosis (MS) is a disease of the central nervous system. MS is an inflammatory, demyelinating disease that affects more than 2 million people worldwide. MS can primarily affect the white matter (WM) and grey matter in the brain and the spinal cord. MS can result in neuronal and axonal degeneration, which can be observed as brain lesions or plaques, grey matter atrophy, and diffuse abnormalities. MS manifest itself in a number of different forms, including: clinically isolated syndrome, relapsing-remitting syndrome, secondary progressive syndrome, primary progressive syndrome, and progressive relapsing syndrome. Damage caused to the brain by MS or other neurodegenerative diseases can make it difficult to perform tractography to determine brain connections, which can limit the usefulness of tractography in clinical evaluation of patients with neurodegenerative diseases.

SUMMARY OF THE DISCLOSURE

The following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure discusses systems and methods for identifying biomarkers that can help with the diagnosis, prognosis, and treatment choices of patients with brain diseases, including demyelinating or neurodegenerative diseases, stroke or brain trauma. Patients can be evaluated using clinical scales, but the scales can be based on patient questionnaires making them an unreliable measure between patients and over the course of the patient's disease progression. Diffusion based magnetic resonance imaging (dMRI) techniques often use parameters such as fractional anisotropy (FA), mean diffusivity (MD), and radial diffusivity (RD) that are based on simple models that can fail in the presence of neurodegeneration, such as demyelination. The present disclosure discusses systems and methods that enhance dMRI images and enable tractography to be performed on images of a damaged nervous system. The damaged tracks identified by the present system can be used as a biomarker for the assessment of patients. In some implementations, the biomarkers are converted into clinical scales that can be used to compare patients to one another or a patient over time.

Figure 1:
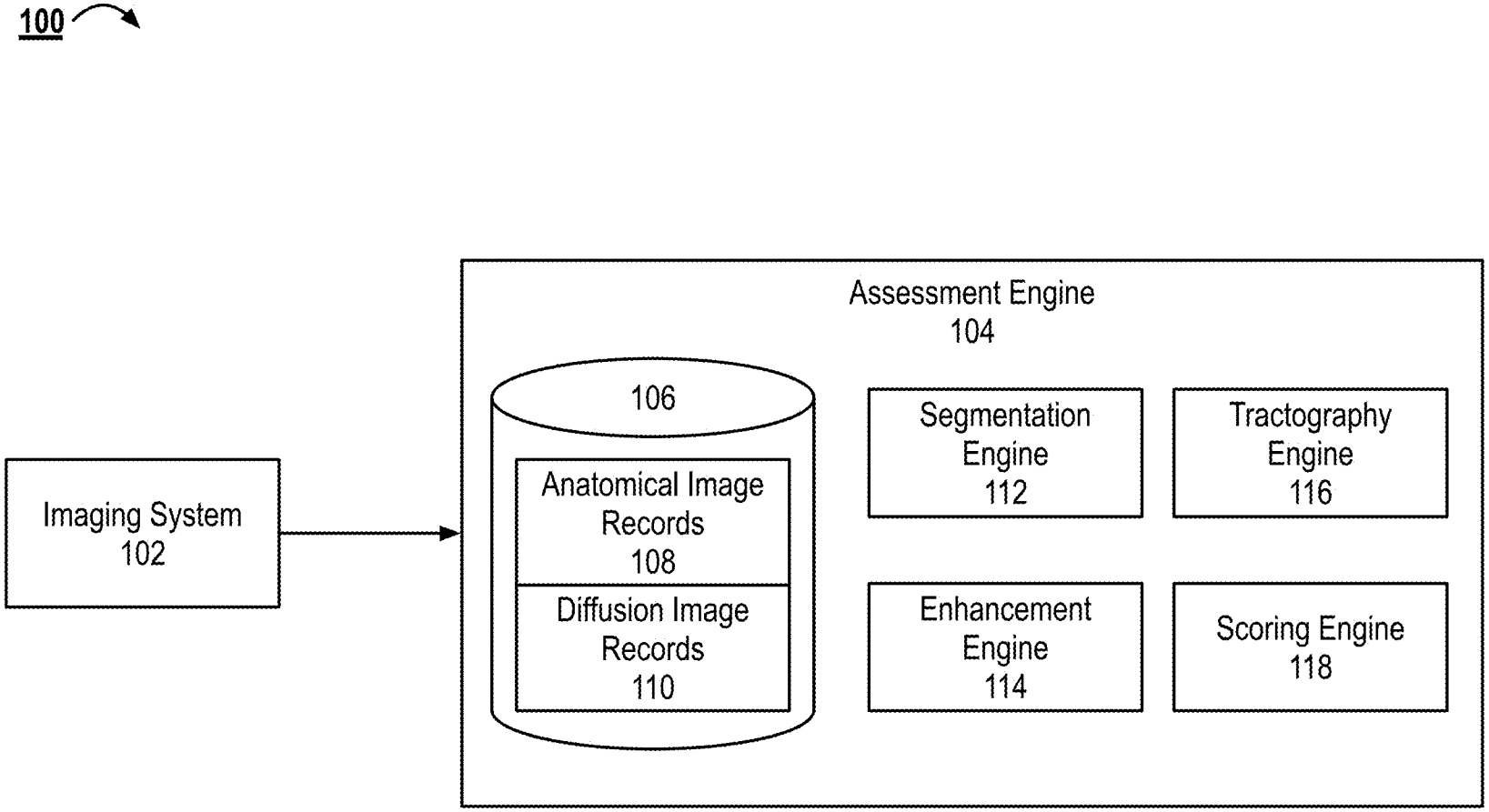
FIG. 1 illustrates a block diagram of an example system for the assessment of neurological damage.

FIG. 1 illustrates a block diagram of an example system 100 for the assessment of neurological damage. The system 100 includes an imaging system 102. The imaging system 102 provides imaging data to the assessment engine 104. The assessment engine 104 includes a database 106 for the storage of anatomical image records 108 and diffusion image records 110. The assessment engine 104 includes a segmentation engine 112, an enhancement engine 114, a tractography engine 116, and a scoring engine 118. In some implementations, the assessment engine 104 can be coupled to a monitor or other system for the display of the results generated by the assessment engine 104.

The system 100 includes the imaging system 102 that provides imaging data to the assessment engine 104. The imaging system 102 can be one or more magnetic resonance imaging (MRI) systems. The imaging system 102 can be configured to acquire imaging data using different imaging acquisition modalities. The imaging system 102 can be configured to capture and generate both anatomical image records and diffusion image records. For example, the imaging system 102 can acquire T1, T2, high-angular resolution diffusion images (HARDI), function MRI (fMRI), magnetization-prepared rapid gradient-echo (MPRAGE), fluid-attenuated inversion recovery (FLAIR), diffusion tensor imaging (DTI), diffusion spectrum imaging (DSI), and optical coherence tomography (OCT), spectroscopy or any combination thereof. In other implementations, a first imaging system 102 can capture and generate the anatomical image records and a second imaging system 102 can capture and generate the diffusion image records. In some implementations, the imaging system 102 provides the imaging data directly to the assessment engine 104 through a direct data or network connection. In other implementations, the imaging system 102 can provide the imaging data to the assessment engine 104 through an intermediary device. For example, the imaging system 102 can first provide the imaging data to an intermediary device such as a networked server, cloud based storage, or other computer, and the assessment engine 104 can retrieve the imaging data from the intermediary device prior to the analysis of the imaging data by the assessment engine 104.

The system 100 also includes the assessment engine 104. The assessment engine 104 and its components are described in greater detail below. As an overview, the assessment engine 104 can receive neurological imaging data (in the form of anatomical image records and diffusion image records), enhance the imaging data, and generate a score to quantify the level of neurological damage experienced by the patient. For example, and using MS as an example disease, the assessment engine 104 can generate a score that relates to the amount of white matter tracts affected by MS lesions. The system 100 can also be used with patient suffering (or believe to be suffering) from Alzheimer's disease, Parkinson's disease, dementia, any other brain disease that presents in the MM with lesional change of gray scale intensity in the corresponding Mill image. In some implementations, the level of damage is converted to a clinical score, such as the Expanded Disability Status Scale (EDSS), Sloan score, multiple sclerosis functional composite (MSFC), paced auditory serial addition test (PASAT), brief repeatable battery-Neuropsychology (BRB-N) test, selective reminder test (SRT), symbol digit modality test (SDMT), spatial recall test, and the word list generation (WLG) test. The lesions change the diffusion properties of the tissue that affect the fiber tracking parameters and result in incorrect streamline reconstruction compared to the underlying anatomy. For example, when a fiber enters a brain lesion the traditional techniques have difficulty in determining whether the fiber continues through the lesion or stops. In some implementations, the techniques have difficulty because the values of the tracking are abnormal in the lesion area the fiber can continue in a random direction introducing an error that will propagate through the fiber tracking algorithm. Because these techniques cannot determine whether the track continues through or stops in the lesion, the techniques cannot accurately calculate fiber track damage caused by the lesion. The assessment engine 104 can improve the analysis of the areas containing lesions and plaques to generate improved tractography through the damaged areas so that the impairment can be assessed.

In some implementations, the assessment engine 104 is a stand-alone device and in other implementations the assessment engine 104 is a component of another device. As a stand-alone device, the assessment engine 104 can include special purpose logic circuitry (e.g., a field programmable gate array (FPGA) or an application specific integrated circuit (ASIC)), a microprocessor, or a combination thereof. The assessment engine 104 can be coupled with a computer or imaging system 102 via a wired or wireless network connection or other wired or wireless connections, such as, but not limited to, a universal serial bus (USB) connection, FireWire connection, eSATA connection, or Thunderbolt connection. When provided with imaging data, the stand-alone assessment engine 104 can return a score for the patient or other result as described herein. In other implementations, the assessment engine 104 can be implemented as a component of the imaging system 102 or other system, such as a desktop computer, and one or more components of the assessment engine 104 can be implemented as components of the other system.

The assessment engine 104 includes the database 106. The database 106 can be stored on a computer readable medium such as, but not limited to, a magnetic disk hard drive, random-access memory (RAM), electrically-erasable ROM (EEPROM), erasable-programmable ROM (EPROM), flash memory, optical media, or any other suitable medium for storing the anatomical image records 108, the diffusion image records 110, and processor executable instructions.

The assessment engine 104 stores anatomical image records 108, diffusion image records 110, and other types of MRI images within the database 106. The anatomical image records 108 can include T1 and T2 images from the imaging system 102. The diffusion image records 110 can include HARDI and other diffusion-weighted images from the imaging system 102.

Figure 2:
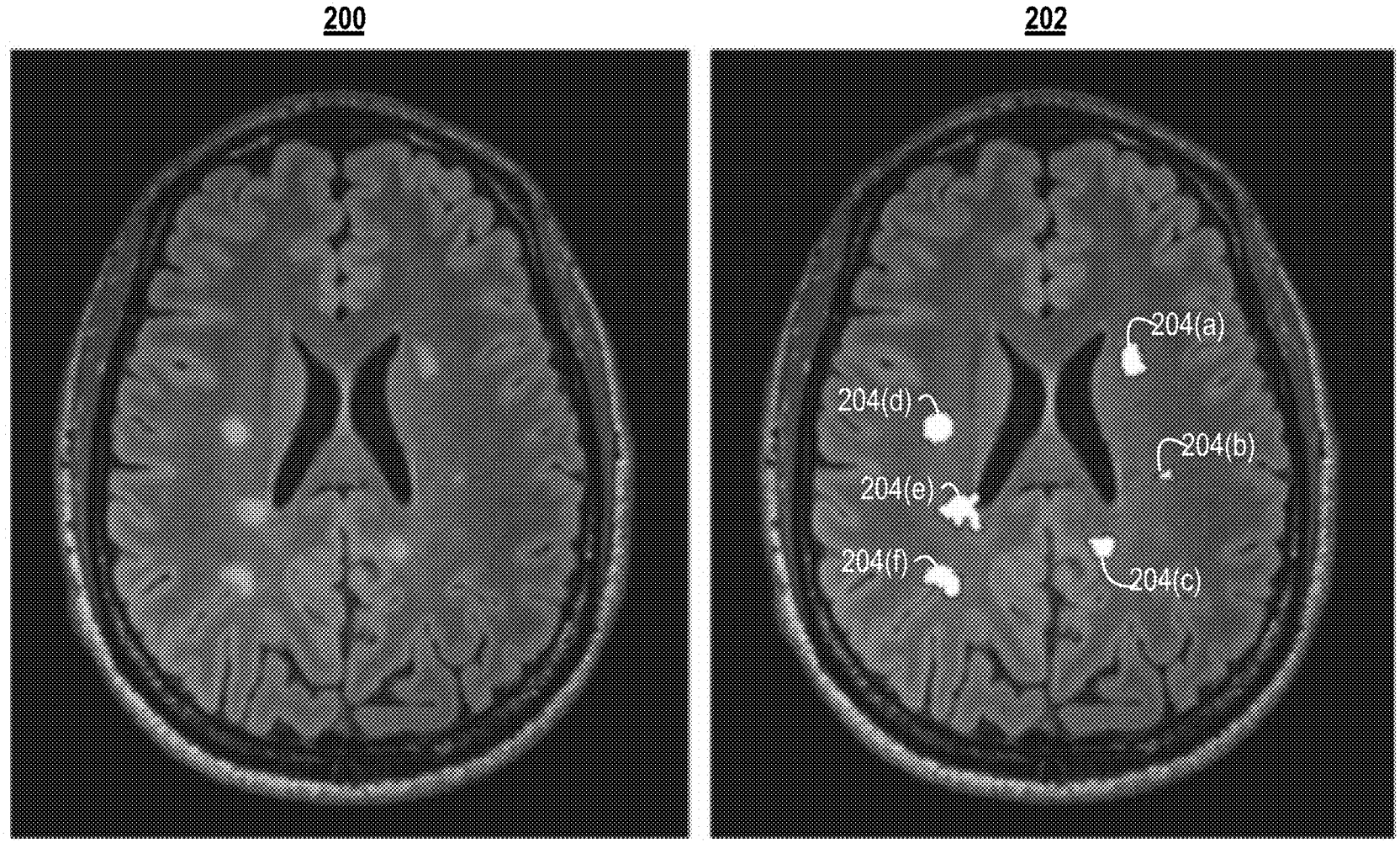
FIG. 2 illustrates an input anatomical image and a segmented anatomical image processed with the system illustrated in FIG. 1.

The assessment engine 104 also includes the segmentation engine 112. As an overview, the segmentation engine 112 segments the anatomical image records 108. In some implementations, the segmentation engine 112 can segment different portions of the anatomical image records 108. For example, the segmentation engine 112 can identify portions of the anatomical image record 108 that correspond to the white matter, the grey matter, the skull, other anatomical structures, or any combination thereof. In some implementations, the segmentation engine 112 can also identify lesions within the anatomical image records 108 and generate segments that contain the lesions. In some implementations, the segmentation engine 112 segments the anatomical image record 108 through the use of edge detection algorithms that identify boundary regions between different tissue types imaged in the anatomical image record 108. The segmentation engine 112 can also use threshold-based methods, histogram-based methods, or graph-based methods to segment the data. FIG. 2 illustrates an example output of the segmentation engine 112. In some implementations, the segmentation engine 112 identifies and segments the brain lesions in a fully automated manner. In other implementations, the segmentation engine 112 can identify and segment the brain lesions in a semi-automated manner. For example, a user may identify the center (or other portion) of a brain lesion and then the segmentation engine 112 can identify the boundary of the lesion. In some implementations, the segmentation engine 112 can store the boundary coordinates of the lesion or an identification of the voxels corresponding to the lesion as a file in the database 106. In some implementations, the coordinates of multiple lesions are stored in separate files or as separate vectors within a single file.

FIG. 2 illustrates an input anatomical image 200 and a segmented anatomical image 202. The anatomical image 202 is a T2 image that includes hyperintensities corresponding to MS lesions. The anatomical image 202 is the output of the segmentation engine 112. The segmentation engine 112 identified the MS lesions and generated segments 204(a)-204(f), which each include one of the MS lesions. As described above, in some implementations, the output of the segmentation engine 112 is an array of vectors that define the boarder of the segments 204(a)-204(f) or an indication of the voxels contained in the segments 204(a)-204(f).

Referring to FIG. 1, the assessment engine 104 also includes the enhancement engine 114. As an overview, the enhancement engine 114 enhances the diffusion image record 110 such that the tractography engine 116 can track or estimate the correct fiber architecture even in the presence of lesions and other neurological damage. The enhancement engine 114 retrieves one or more of the diffusion image records 110 from the database 106. In some implementations, the diffusion image records 110 are initially modeled as fiber orientation distribution functions (FOF) or spherical harmonics (SH) glyphs. The enhancement engine 114 converts the glyphs into an amplitude image by sampling the glyphs from a plurality of directions to generate a voxel from each glyph that defines the intensity of the diffusion along the plurality of directions. In some implementations, the glyphs are sampled along between about 100 and about 500, about 100 and about 400, about 100 and about 300, or about 100 and about 200 directions.

In some implementations, the enhancement engine 114 masks the amplitude image with a white matter mask. In the below described convolution step, the white matter mask can prevent the ventricles and the exterior of the brain from being included in the convolution.

The enhancement engine 114 is also configured to generate a kernel. The enhancement engine 114 can convolve the masked, amplitude image with the generated kernel. The kernel can solve the diffusion equation for diffusion MRI images. The kernel represents the Brownian motion kernel on the coupled space of positions and orientations:

$$p_{3D}^{D_{33},D_{44},t}((x, y, z)^T, n(\beta, \gamma)) \approx N(D_{33}, D_{44}, t) \cdot p_{2D}^{D_{33},D_{44},t}((z/2, x), \beta) \cdot p_{2D}^{D_{33},D_{44},t}((z/2, -y), \gamma)$$

where:

$$y = (x, y, z)^T$$

$$N(D_{33}, D_{44}, t) \approx \frac{8}{\sqrt{2}} \sqrt{\pi}\, t \sqrt{tD_{33}} \sqrt{D_{33}D_{44}}$$

provides that the total integral over positions and orientations is 1. The 2D kernel is given by:

$$p_{2D}^{D_{33},D_{44},t}(x, y, \theta) \equiv \frac{1}{32\pi^2 c^4 D_{44} D_{33}} e^{-\frac{\sqrt{EN((x,y),\theta)}}{4c^2 t}}.$$

Where the short notation is:

$$EN((x, y), \theta) = \left(\frac{\theta^2}{D_{44}} + \frac{\left(\frac{\theta y}{2} + \frac{\theta/2}{\tan(\theta/2)} x\right)^2}{D_{33}}\right)^2 + \frac{1}{D_{44}D_{33}}\left(\frac{-x\theta}{2} + \frac{\theta/2}{\tan(\theta/2)} y\right)^2.$$

In some implementations, to avoid numerical errors:

$$\frac{\theta/2}{\tan(\theta/2)} = \frac{\cos(\theta/2)}{1 - (\theta^2/24)} \text{ for } |\theta| < \frac{\pi}{10}$$

The diffusion parameters $D_{33}$, $D_{44}$, and the stopping time t allow the adaptation of the kernels to different patients. In some implementations, t determines the relevance of the neighborhood; $D_{33}$ determines the kernel width; and the quotient $D_{44}/D_{33}$ models the bending of the fibers along which diffusion takes place.

The enhancement engine 114 can then convolve the kernel with the masked, amplitude image (U):

$$\phi(U)[y, n_k] = \sum_{y' \in P} \sum_{n' \in T} P_{y,n_k}(y', n')U(y', n')\Delta y' \Delta n'$$

Where $p_{y,nk}$ is the kernel at position y and orientation $n_k$; $\Delta y'$ is the discrete volume measure; $\Delta n'$ is the discrete surface measure; P is the set of lattice position neighboring y; and T is the set of tessellation vectors. The rotated and translated correlation kernel is:

$$p_{y,n_k}(y',n') = p_{3D}^{D_{33},D_{44},t}(R_{n'}^{-1}(y'-y), R_{n'}^{-1}n)$$

Where $R_{n'}$ is any rotation mapping onto n'.

In some implementations, the enhancement engine 114 tunes the kernel to the patient or to a class of patient (e.g., to a type of manifestation of the disease or a specific disease), and in other implementations, the enhancement engine 114 uses the same kernel parameters for each patient. The enhancement engine 114 may tune the kernel by setting the parameters $D_{33}$, $D_{44}$, t, or any combination thereof. For example, $D_{33}$ can be between about 1 and about 2, $D_{44}$ can be between about 0.001 and about 0.05, and t can be between about 1 and about 20.

In some implementations, the enhancement engine 114 is configured to calculate voxel scattering coefficient (VSC). In some implementations, the VSC is calculated before the above-described kernel is applied and the kernel can be updated responsive to the VSC. The VSC can be an estimate of the number and distribution (or clustering) of the patient's lesions. For example, if the VSC is high, the voxels are very spread (maybe forming small and separated lesion groups). If the VSC is low, the voxels are concentrated, suggesting a relatively larger group of lesions or a number of clustered small lesion. The VSC can be calculated by calculating a matrix of covariances in the x, y, and z direction among the positions of all the voxels. The enhancement engine 114 can then calculate the determinate of the matrix. The VSC can be the summer of all the voxels divided by the determinant.

Figure 3A:
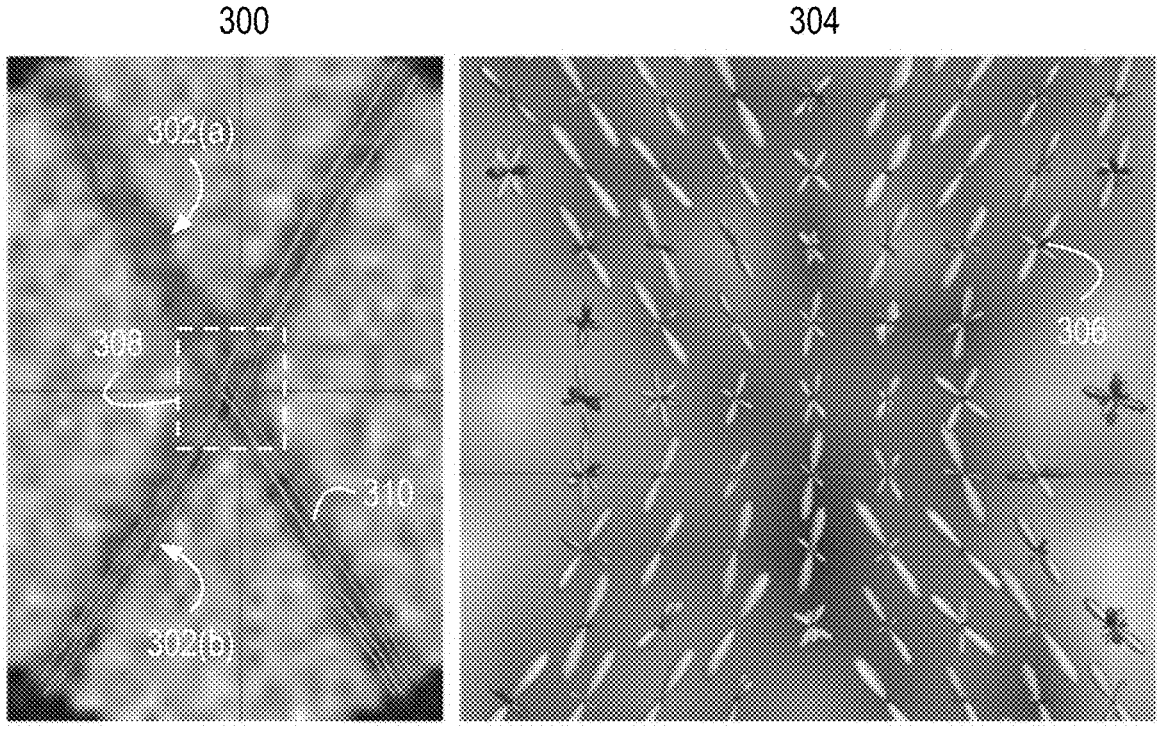
FIGS. 3A and 3B illustrate a tractography image and an orientation distribution function (ODF) glyph image of numerically generated phantom data mimicking crossing nerve bundles before and after processing with the enhancement engine of the system illustrated in FIG. 1.
Figure 3B:
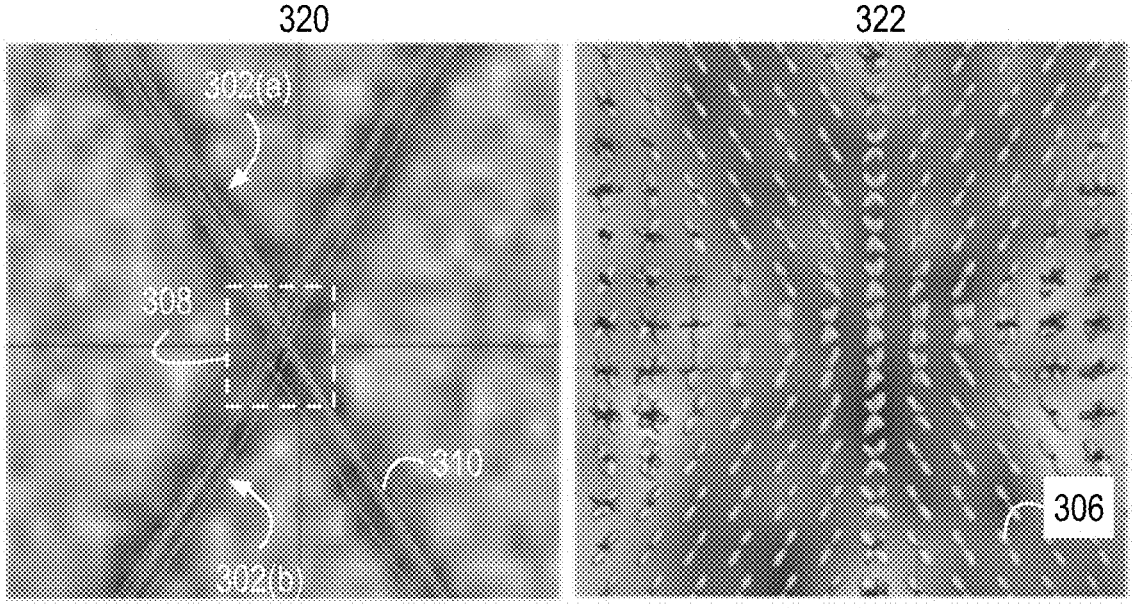

FIGS. 3A and 3B illustrate a tractography image and an ODF glyph image of crossing phantom nerve bundles with and without, processing with the enhancement engine, respectively. FIG. 3A illustrates a tractography image 300 with a first nerve bundle 302(a) and a second nerve bundle 302(b) crossing at about 60 degrees. The corresponding glyph image 304 illustrates the glyphs 306 present at the intersection 308 of the first nerve bundle 302(a) and second nerve bundle 302(b) in the tractography image 300. As described below, the tractography engine 116 identifies tracks responsive to the glyphs 306. In the tractography image 300 (which was not processed by the enhancement engine 114), the tractography engine 116 identifies a plurality of tracks 310. As illustrated in the tractography image 300, a bundle of fibers 310 (e.g. a track) starts in the lower right-hand corner of the tractography image 300 and projects towards the upper left-hand corner of the tractography image 300. The crossing of the first nerve bundle 302(a) and the second nerve bundle 302(b) create a conflictive point at the intersection 308, and, as illustrated, a number of the tracks 310 incorrectly terminates at the intersection 308.

FIG. 3B illustrates a tractography image 320 of the first nerve bundle 302(a) and the second nerve bundle 302(b) crossing at about 60 degrees after processing with the enhancement engine 114. The corresponding glyph image 322 illustrates the glyphs 306 present at the intersection 308 of the first nerve bundle 302(a) and second nerve bundle 302(b) in the tractography image 320. As illustrated in the tractography image 320, a bundle of fibers 310 starts in the lower right-hand corner of the tractography image 320 and projects towards the upper left-hand corner of the tractography image 300. In contrast to the tractography image 300, the tracks 310 continue through the intersection 308 and continue projecting toward the upper left-hand corner of the tractography image 320.

Referring to FIG. 1, the assessment engine 104 also includes a tractography engine 116. As discussed briefly above, the tractography engine 116 analyzes the enhanced image output by the enhancement engine 114 and estimates neural tracks in the enhanced image. The tractography engine 116 models tracks (e.g., bundles of axons) that connect different regions of the brain. The tractography engine 116 models the tracks based on the diffusion of water molecules within the brain and the enhanced image to generate a mask estimating where fibers would be if there were no lesions or damage. In some implementations, the tractography engine 116 uses streamline tractography to represent the underlying neural fibers. In general, the tractography engine 116 can use fiber-orientation descriptive models to find paths of minimal hindrance to water diffusion using local voxel-wise orientation information. The tractography engine 116 can model the tracks by calculating an orientation estimate at each voxel within the enhanced image. In some implementations, the tractography engine 116 can generate tracks responsive to seed locations. The seed locations can serve as a beginning location of interest, and the tractography engine 116 can identify tracks that begin at or near the seed locations. The seed locations can be provided to the tractography engine 116 by a user of the system 100 or the seed locations can be automatically determined. For example, to determine the tracks of the optic radiations, the seed location can be the thalamus, which can be identified using a gray and white matter mask. In some implementations, inclusion locations can also be used by the tractography engine 116 to refine the generated tracks. For example, tracks starting from the seed location that do not pass through inclusion locations can be discarded by the tractography engine 116. Using the visual cortex an example inclusion location and continuing the above example of determining the tracks of the optic radiations, tracks that don't pass through the visual cortex can be discarded. The inclusion locations can be areas along the path of the tracks or a termination location of the tracks.

In some implementations, the tractography engine 116 can filter identified fibers and remove spurious fibers from the tracks. The tractography engine 116 can remove fibers from the tracks based on fiber length. For example, fibers that are shorter or longer than a predefined range may be excluded from the track. In another example, fibers that deviate in length from the track's average length a predetermined amount can be excluded.

In another example, the tractography engine 116 can filter the identified fibers using a centroid. The centroid of each fiber can be calculated to determine a position (x, y, z) for the fiber. Each of the coordinates can be compared with the distribution of all coordinates in the bundle. For example, the x position of a fiber centroid is compared with the x position distributions for all the centroids. A thresholds $T_x$ can be defined for the x coordinate. If x differs more than $T_x$ standard deviations from the mean x, the fiber can be discarded. The process can then be repeated for they and z coordinates with their respective thresholds $T_y$ and $T_z$.

In another example, the tractography engine 116 can filter the identified fibers using coherence. The tractography engine 116 can estimate each fibers coherence by computing the increments in x, y, and z between each pair of adjacent point: incX, incY, incZ along the fiber's path. The tractography engine 116 can then compare the distribution of incX with the distribution of incX for all the fibers. The two distributions can be compared with a Kolmogorov Smirnov test to obtain a p-value. If the p-value is lower than a given threshold, the fiber can be discarded. The process can be repeated for they and z coordinates.

In some implementations, one or more of the filtering methods can be used in combination with one another. For example, first the fibers can be filtered using the coherence method. The remaining fibers can be further filtered using the fiber length method, and the remaining fibers can be further filtered using the centroid method. In some implementations, the filtering process can be repeated a predetermined number of times.

Figure 4:
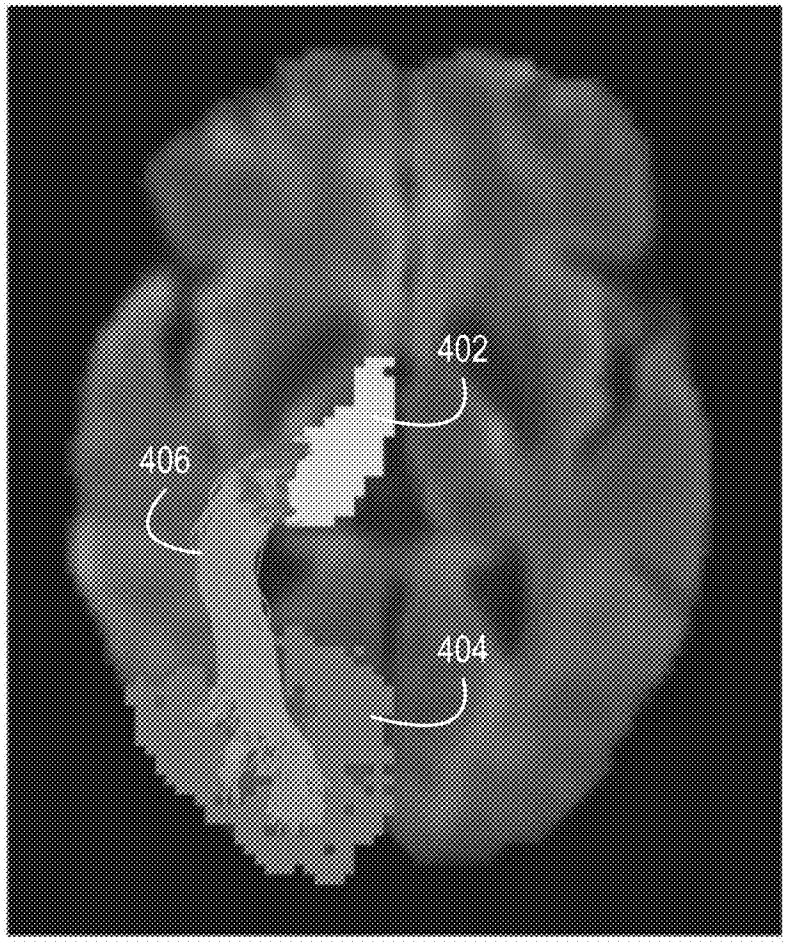
FIG. 4 illustrates an example tractography image generated by the tractography engine of the system illustrated in FIG. 1.

FIG. 4 illustrates an example tractography image 400 generated by the tractography engine 116. As described above, the tractography engine 116 determines or is provided with a seed location from which the tracks are to start. To identify the tracks starting in the thalamus and ending in the visual cortex, in the tractography image 400, the thalamus 402 is selected as the seed location. In order to increase segmentation, the region of interest can be divided into multiple portions (e.g., into 4 parts). The center of mass can be estimated for each and the exterior-posterior portion is preserved where the seeding is to be done. The minimum cube that fits both seed and include region can be found and then all the cortical regions except the regions of interest are subtracted. The generated mask can be set to 1 outside the cube and inside the other cortical regions so that all fibers trespassing that mask will be excluded. The visual cortex 404 is selected as an inclusion location. Responsive to the identification of the seed location and the inclusion location, the tractography engine 116 identifies the tracks 406 traveling from the thalamus to the visual cortex.

Referring to FIG. 1, the assessment engine 104 also includes the scoring engine 118. The scoring engine 118 can generate one or more clinical scores for the images. To determine the amount of track damage the scoring engine 118 can register the segmented anatomical image with the tractography image. For the volumetric scores, the tractography is converted into a mask and registered to the anatomical image. The score can correspond to the volume or number of damaged tracks. The volumetric score can correspond to the percent of volume or the volume in the anatomical space. For the fiber-based scores, the lesions mask is registered to the diffusion space and then the score is computed. The score can correspond to the volume or number of damaged fibers (or tracks).

In some implementations, the lesion mask is registered with the tractography image by finding the lesions in the anatomical space (T1 or T2). The reference image (T1 or T2)

is registered into the respective subject image (T1 or T2), and the same transformation is applied to the lesion mask so that now the lesion mask is in the same space as the subject. In some implementations, the tractography mask image can be registered into the lesion mask (in T1 or T2 space) in order to have more precision due to T1 space higher resolution.

Once the images are registered, the damage to the tracks can be converted to damage scores and clinical scores. In some implementations, damaged tracks are those that pass through one of the lesion segments. The damage score can be the percentage of tracks in a bundle that are damaged. For example, if 20% of the tracks from the thalamus of the visual cortex pass through a lesion then the score can be 20%. In another implementation, the score can be based on the volume of a lesion inside a bundle. The volume can be determined by the number of lesion voxels within the bundle divided by the volume of the bundle. In some implementations, a total score can be generated for the patient by combining the scores from different pathways. For example, the score from the corpus callosum, optical radiation, and corticospinal tract can be combined to generate a single score. In some implementations, the score assessing the level of damage can be converted into a clinical score, such as a Sloan score, EDSS score, or other above described clinical scores.

Figure 5:
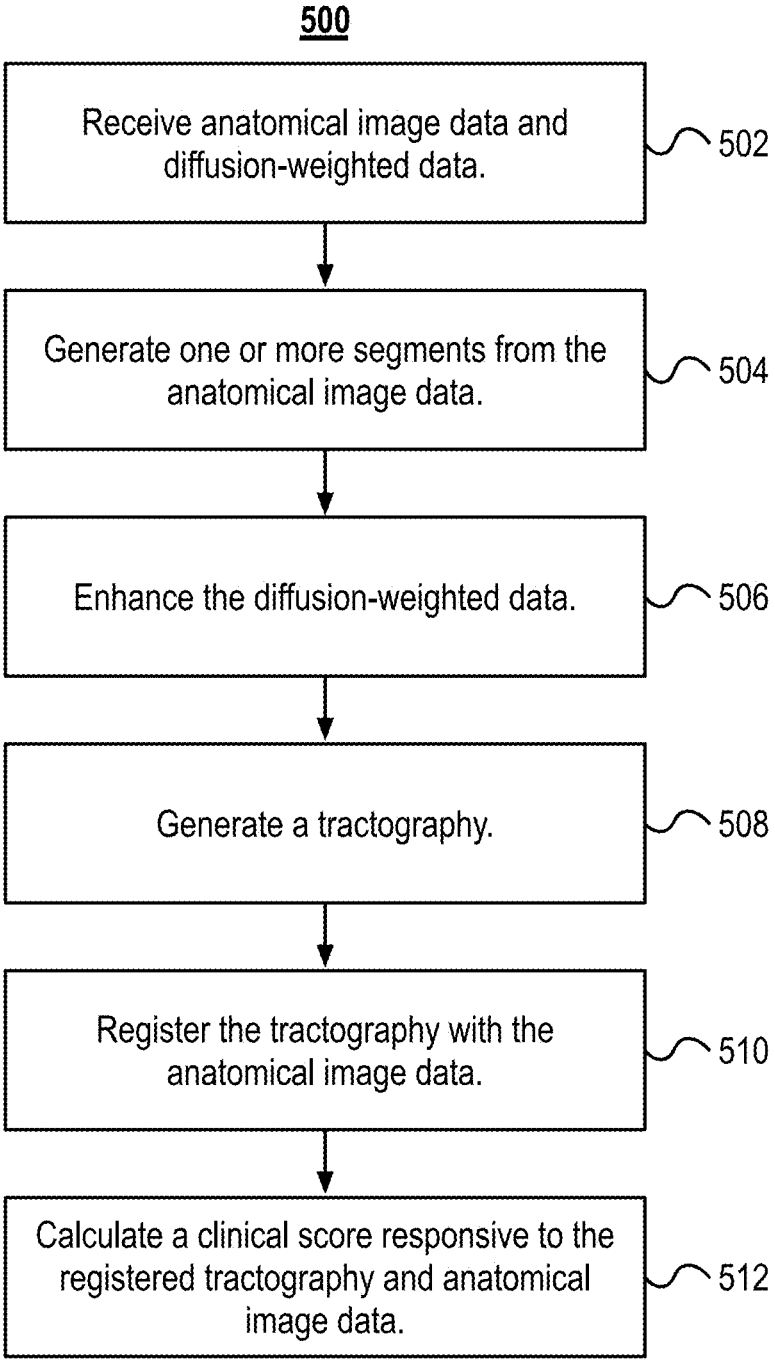
FIG. 5 illustrates a block diagram of an example method for calculating a clinical score using the system illustrated in FIG. 1.

FIG. 5 illustrates a block diagram of an example method 500 for calculating a clinical score or a damage score (or more simply, a score). The method 500 includes receiving anatomical and diffusion-weighted (DW) data (step 502). The method 500 also includes generating one or more segments from the anatomical image data (step 504). The method 500 includes enhancing the DWI data (step 506), and generating a tractography (step 508). The generated tractography is registered with the anatomical image data (step 510). A score is calculated responsive to the registered tractography and anatomical image data (step 512).

As set forth above, the method 500 includes receiving anatomical image data and DWI data (step 502). Also referring to FIG. 1, the anatomical image data and the DWI data can be received by the assessment engine 104 from an imaging system 102 or from an intermediary device, such as networked or cloud based storage. In some implementations, the received anatomical data can include 3D structural T1-Magnetization-Prepared-Rapid-Gradient-Echo (MPRAGE) data with a voxel size of about 0.9×0.9×0.9 $mm^3$. The anatomical data can also include 3D Structural Fluid Attenuated Inversion Recovery (FLAIR) data with a voxel size of about 0.9×0.9×0.9 $mm^3$. The DWI data can include High-Angular Resolution Diffusion Imaging (HARDI), with a voxel size of about 2×2×2 $mm^3$, b-value of 1500 $s/mm^2$, and about 70 gradients. The resolution of the data received by the assessment engine 104 can be of greater or less than the above described resolution. The received image data can be stored by the assessment engine 104 into the database 106.

The method 500 can also include generating one or more segments from the anatomical data (step 504). In some implementations, each of the segments can include a lesion. The segment can identify the two-dimensional or three-dimensional area, boarder location, or volume within the anatomical images that is occupied by lesions or plaques. In some implementations, the assessment engine 104 is configured to display the anatomical images to a user. The user can interact with the anatomical images and outline the lesions or plaques to generate the boarders of the segments. In other implementations, the segments are automatically generated using, for example, the FreeSurfer© software (made available by FreeSurfer, of Cambridge, Mass.). The location of each of the segments can be stored into the database 106 in association with the anatomical image. For example, an identifier of the volumes contained within each of the segments can be stored. In other implementations, the segmentation process is semi-automated and the user identifies the lesion (or a lesion of interest) and the assessment engine can then identify the boarder of the lesion.

The method 500 can also include enhancing the DWI data (step 506). As described above in relation to FIGS. 3A and 3B and FIG. 1, in some implementations, unenhanced DWI data in patients with plaques can result in tractography that incorrectly terminates at intersections or other conflict points such as lesions. The enhancement engine 114 of the assessment engine 104 can enhance the DWI data such that the tractography engine 116 can properly generate tracks that pass through intersections, lesions, and other conflict points. In some implementations, the enhancement engine 114 enhances the DW data by convolving the DW data with the above described kernel. The enhancement engine 114 can tune the kernel to the patient's data prior to convolving the DW data with the kernel. For example, the enhancement engine 114 can tune the $D_{33}$, $D_{44}$, and t parameters of the kernel. In some implementations, different regions of the DW data can be convolved with different kernel settings. In some implementations, $D_{33}$ is between about 0.7 and about 5, between 0.8 and about 3, or between about 0.9 and about 1.2; $D_{44}$ is between about 0.02 and about 0.08, between about 0.03 and about 0.07, or between about 0.04 and about 0.06; and t is between about 1 and about 20, between about 1.2 and about 10, between about 1.3 and about 5, or between about 1.3 and about 1.6.

The method 500 also includes generating a tractography (step 508). Also referring to FIG. 1, the tractography engine 116 receives the enhanced image from the enhancement engine 114. In some implementations, the tractography engine 116 also receives one or more seed locations and one or more inclusion locations. Given the seed locations and the inclusion locations, the tractography engine 116 can determine which tracks begin in the seed locations and then pass through or terminate in the inclusion locations. In other implementations, the tractography engine 116 can generate the tractography based on a template. The template can be generated by the tractography engine 116 based on tractographies from healthy individuals (e.g., individuals that do not have brain lesions or other damage). In some implementations, the tractography engine 116 can generate the template tractography by selecting and merging together tractographies form health individuals that are similar to the patient in race, weight, height, sex, age, or any combination thereof.

The method 500 also includes registering the tractography with the anatomical image (step 510). In order to compare the tractography results with anatomical information (eg. the lesion mask) the tractography and anatomical image are overlapped into the same space. In some implementations, the anatomical image and segments are registered with the above-described template and in other implementations the anatomical image is registered with the tractography made for the patient as described in relation to step 508. In some implementations, the anatomical image is registered to the enhanced DWI using non-linear registration.

In some implementations, to maintain the tractography, the anatomical image can be moved to the same space as the tractography (e.g., the b0 space). In some implementations, the anatomical image can be a T1 image. The registration can include moving a specific anatomical image in T1 space (e.g., the skull-stripped T1 image itself) to an image in the b0 space. The method 500 can include generating a transformation matrix that is employed to move the desired anatomical image (e.g., lesion mask) to the b0 space. Once this is done tractography and lesions are in the same space and can be compared. In some implementations, this method can be used in cases to evaluate the damage as a percentage of fibers that traverse a lesion because the spatial position of each fiber in the tractography is needed. In some implementations, a predetermined amount of the fiber must be damaged before the fiber is classified as damaged.

In another implementation, the tractography is converted into an image for registration with the lesion maps. In these implementations, the resulting image can be to the T1 space. The image can be generated by creating an empty (all zeros) 3D image. The 3D image can have the same dimensions as the image from which the tractography came from. The tractography is composed by a series of fibers, each composed by an ordered series of points (e.g., a x, y, and z coordinate). For each fiber and each point in the fiber, a "1" is added to the voxel value corresponding to that space location in the newly generated 3D image. The process is repeated for all of the points in all of the fibers. Once repeated for each fiber, each voxel has a value that indicates the number of fibers that have pass through the voxel in the tractography. The resulting image is in the b0 space and can be registered to other spaces The method 500 also includes calculating a score responsive to the registered tractography and anatomical image data (step 512). The clinical score can be responsive to a damage score calculated by the scoring engine, which can be converted into a clinical score using a linear correlation or a neural network. In some implementations, the scoring engine can calculate the damage score as the number of lesioned voxels within a brain track (e.g., the number of voxels within the lesion segments) divided by the total number of voxels within the brain track. In another implementation, the damage score can be calculated as the damage density divided by the bundle density. The damage density can be the sum of the voxels in the registered tractography that are located within one of the voxel segments and the bundle density can be the total sum of the voxels in the tractography.

In some implementations, the amount of damage is calculated as the number of fibers that traverse a lesion. In these implementations, the lesion mask and tractography are placed in the same space by moving the anatomical lesion mask into the space of the tractography. Then, for each fiber of the tractography, the position (x, y, z) of every point of the fiber is checked to determine whether the voxel in the lesion mask corresponds to the position of a lesion. If the checked point and the lesion have the same position, then the fiber can be flagged as damaged. After analyzing all the fibers, the number of damaged fibers is divided by the total number of fibers and then multiplied by 100 to obtain a percentage of damage. In some implementations, a predetermined number of fiber points (or a percentage of the points of a fiber) have to be flagged as damaged before the fiber is flagged as damaged.

In some implementations, the amount of damage is calculated as the percent of damaged volume. In these implementations, the lesions and tractography are placed in the same space by converting the tractography into a 3D image. As described above, each voxel value reflects the number of fibers traversing or visiting that location of space. In these implementations, the 3D image is binarized using a threshold T, which must be >=1. In the binarizing process voxels whose value is >=T are set to 1 and voxels whose value is <T are set to 0. This threshold is used to remove the effect of spurious fibers. The tract volume is calculated as the sum of the voxels in the binarized tractography image. The lesion volume can be calculated by multiplying the lesion mask by the binarized image. The values of all voxels in the resulting image can then be summed. The percentage of damage is calculated as the lesion volume divided by the tract volume multiplied by 100.

In some implementations, the amount of damage is calculated as a probabilistic percent of damaged volume. In these implementations, the lesions and tractography are placed in the same space by converting the tractography into a 3D image. The probabilistic percentage of damage is calculated similar to the above described percentage calculation. However, the 3D image is not binarized. Accordingly, the values in the voxels of the 3D image represent the frequency of fibers traversing each point in space. Higher values can provide a higher confidence that the voxel corresponds to the real tract in the patient. Very low values can provide less confidence, and might be caused by spurious fibers in the tractography. The confidence can be converted into a numerical estimation by means of dividing the value in each voxel by the maximum value of all the voxels (M). The result is a 3D tractography image that is a normalized 3D tractography image in which each voxel has a value between 0 and 1. We can understand these values as probabilities that the voxel corresponds to the real tract. The normalized 3D tractography image can be multiplied by the lesion mask to calculate the probabilistic lesion volume. The probabilistic tract volume can be the summer of all the voxels in the normalized 3D tractography image. The probabilistic damage can be calculated as the probabilistic lesion volume divided by the probabilistic tract volume multiplied by 100.

Figure 6A:
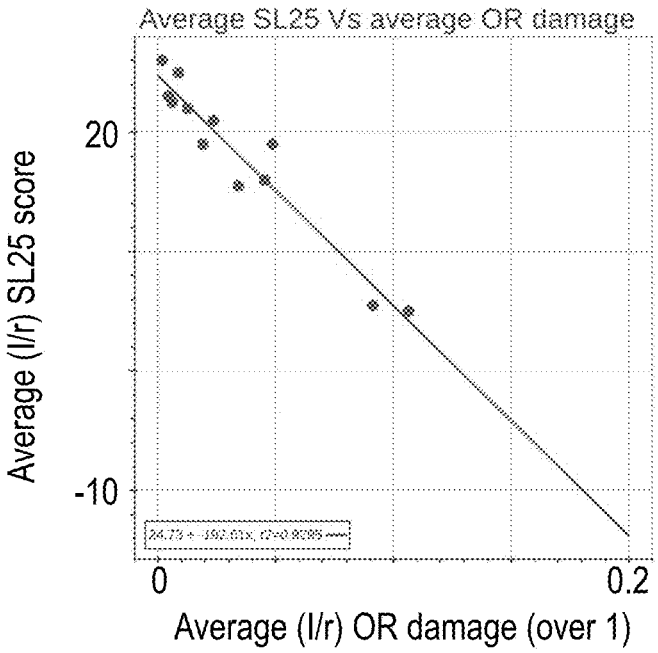
FIGS. 6A-6F illustrate the relationship between the amount of damage detected using the system illustrated in FIG. 1 and the patient's Sloan score.
Figure 6B:
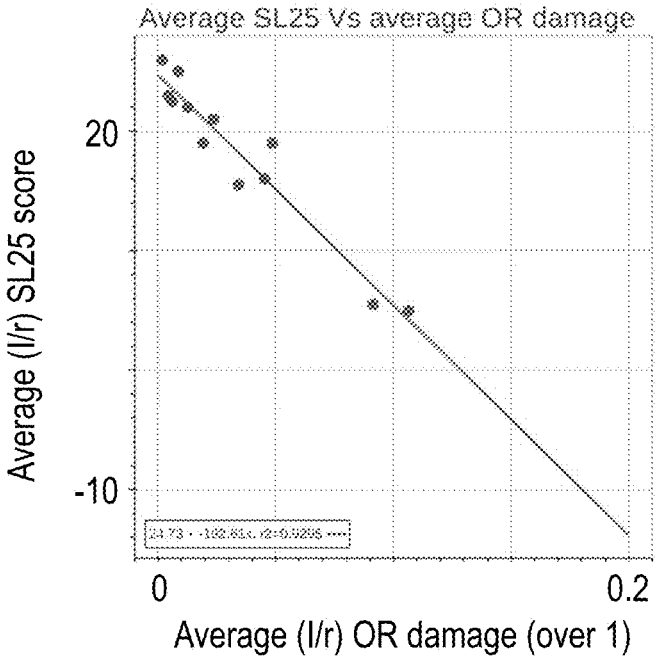
Figure 6C:
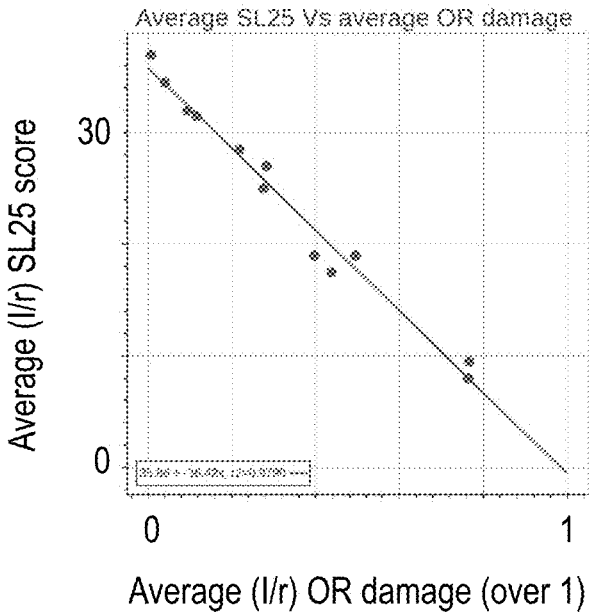
Figure 6D:
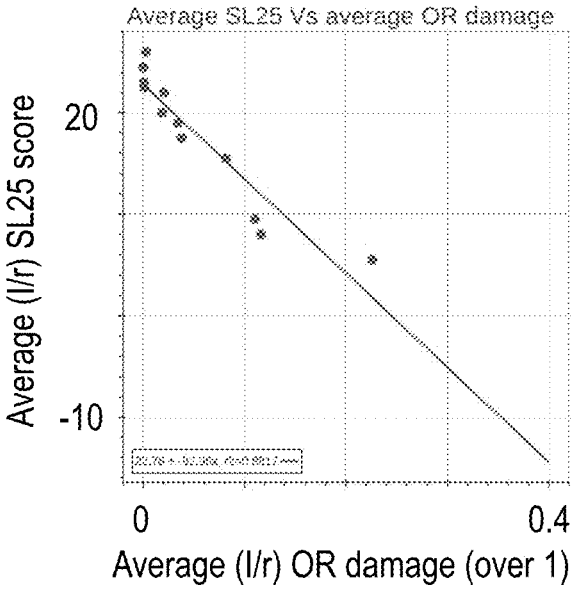
Figure 6E:
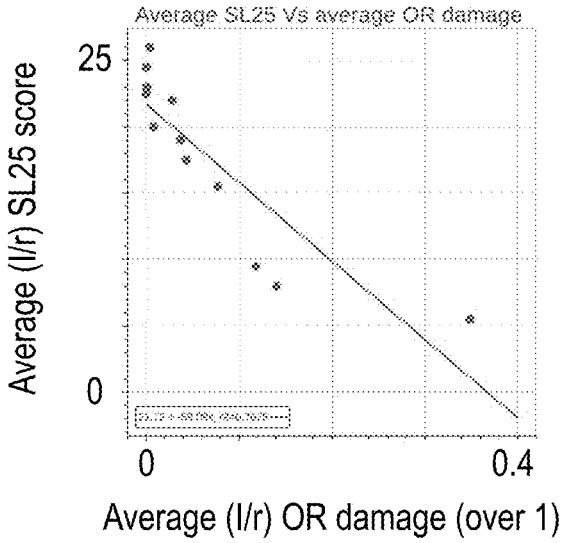
Figure 6F:
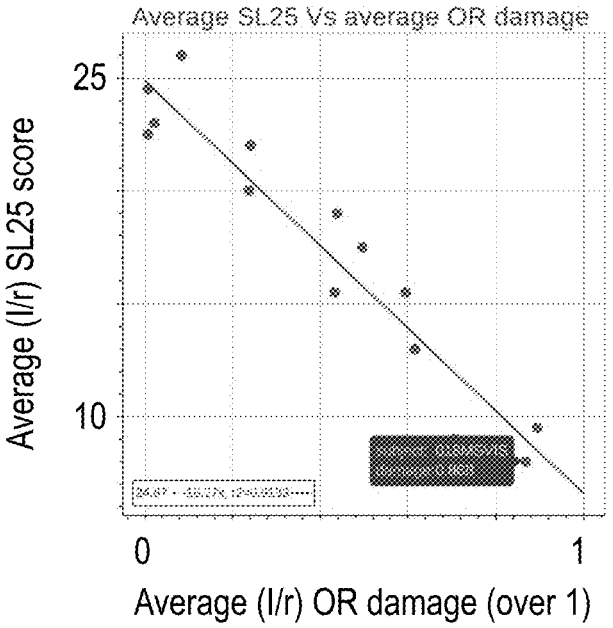

FIGS. 6A-6F illustrate the relationship between the amount of damage detected using the system illustrated in FIG. 1 and the patient's 2.5% low contrast visual acuity (Sloan score). As described above, the amount of damage can be calculated in a number of ways. FIG. 6A illustrates the relationship between the Sloan score and the calculated damage when the damage is calculated as a percentage of damaged volume. FIG. 6B illustrates the relationship between the Sloan score and the calculated damage when the damage is calculated as a probabilistic percentage of damaged volume. FIG. 6C illustrates the relationship between the Sloan score and the calculated damage when the damage is calculated as a percentage of damaged tracks. In FIGS. 6A-6C, the lesion mask is calculated using template mask from a white matter atlas. FIG. 6D illustrates the relationship between the Sloan score and the calculated damage when the damage is calculated as a percentage of damaged volume. FIG. 6E illustrates the relationship between the Sloan score and the calculated damage when the damage is calculated as a probabilistic percentage of damaged volume. FIG. 6F illustrates the relationship between the Sloan score and the calculated damage when the damage is calculated as a percentage of damaged tracks. In FIGS. 6D-6F, the lesion mask is calculated using patient specific lesion masks generated by the systems described herein.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, non-contact interfaces, and digitizing tablets. As another example, a computer may receive input information through speech recognition or in other audible format.

Such computers may be interconnected by one or more networks in any suitable form, including a local area network or a wide area network, such as an enterprise network, an intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents. All publicly available documents referenced herein, including but not limited to U.S. patents, are specifically incorporated by reference.

What is claimed:

1. A method comprising:

receiving anatomical image data and diffusion-weighted data of a patient's nervous system;

generating a segment from the anatomical image data identifying a first volume of voxels;

generating enhanced diffusion-weighted data in the segment responsive to receiving the diffusion-weighted data;

generating a track comprising a second volume of voxels in the enhanced [diffusion-weight] *diffusion-weighted* data;

registering the segment identifying the first volume of voxels with the track in the enhanced [diffusion-weight] *diffusion-weighted* data, the segment located in the same space as the track, the segment configured for comparison with the track comprising the second volume of voxels; and

[calculating] *determining* a damage score [to] *for* the track based on the first volume of voxels, the second volume of voxels, and the segment registered with the track.

2. The method of claim 1, wherein [each of the one or more segments correspond] *the segment corresponds* to damage identified in the anatomical image data.

3. The method of claim 2, wherein the damage comprises at least one of a brain lesion and a plaque.

4. The method of claim 1, wherein generating the enhanced diffusion-weighted data comprises convolving the diffusion-weighted data with a kernel representing Brownian motion.

5. The method of claim 1, wherein the track is one of a corpus callosum, an optical radiation, and a corticospinal tract.

6. The method of claim 1, further comprising generating the track responsive to a track template.

7. The method of claim 1, further comprising determining a number of voxels of the second volume of voxels contained within the segment.

8. The method of claim 7, wherein [calculating] *determining* the damage *score* is [calculated] responsive to the number of voxels of the second volume of voxels contained within the segment and the second volume of voxels.

9. The method of claim 1, further comprising [calculating] *determining* a clinical score responsive to the determined damage to the track.

10. The method of claim 1, wherein the anatomical image data comprises one or more of T1, T2, HARDI, and [Mill] *fMRI* data.

11. A system comprising:

an assessment engine comprising one or more processors and a processor readable medium storing instructions that when executed by the one or more processors cause the one or more processors to:

receive anatomical image data and diffusion-weighted data of a patient's nervous system;

generate a segment from the anatomical image data identifying a first volume of voxels;

generate an enhanced diffusion-weighted data responsive to the diffusion-weighted data;

generate a track comprising a second volume of voxels in the enhanced [diffusion-weight] *diffusion-weighted* data;

register the segment identified as the first volume of voxels with the track in the enhanced [diffusion-weight] *diffusion-weighted* data, the segment located in the same space as the track, the segment configured for comparison with the track comprising the second volume of voxels; and

[calculate] *determine* a damage score [to] *for* the track based on the first volume of voxels, the second volume of voxels, and the segment registered with the track.

12. The system of claim 11, wherein [each of the one or more segments correspond] *the segment corresponds* to damage identified in the anatomical image data.

13. The system of claim 12, wherein the damage comprises at least one of a brain lesion and a plaque.

14. The system of claim 12, wherein the track is one of a corpus callosum, an optical radiation, and a corticospinal tract.

15. The system of claim 11, wherein execution of the instructions further cause the one or more processors to convolve the diffusion-weighted data with a kernel representing Brownian motion to generate the enhanced diffusion-weighted data.

16. The system of claim 11, wherein execution of the instructions further cause the one or more processors to generate the track responsive to a track template.

17. The system of claim 11, wherein execution of the instructions further cause the one or more processors to determine a number of voxels of the second volume of voxels contained within [one of] the segment.

18. The system of claim [11] *17*, wherein execution of the instructions further cause the one or more processors to [calculate] *determine* the damage responsive to the number of voxels of the second volume of voxels contained within [one of] the segment and the second volume of voxels.

19. The system of claim 11, wherein execution of the instructions further cause the one or more processors to [calculate] *determine* a clinical score responsive to the determined damage to the track.

20. The system of claim 11, wherein the anatomical image data comprises one or more of T1, T2, HARDI, and fMRI data.

* * * * *